United States Patent [19]

Radhakrishnan et al.

[11] Patent Number: 5,192,528
[45] Date of Patent: * Mar. 9, 1993

[54] CORTICOSTEROID INHALATION TREATMENT METHOD

[75] Inventors: Ramachandran Radhakrishnan; Paul J. Mihalko, both of Fremont; Robert M. Abra, San Francisco, all of Calif.

[73] Assignee: Liposome Technology, Inc., Menlo Park, Calif.

[*] Notice: The portion of the term of this patent subsequent to Jan. 23, 2007 has been disclaimed.

[21] Appl. No.: 444,360

[22] Filed: Dec. 1, 1989

Related U.S. Application Data

[63] Continuation-in-part of Ser. No. 22,937, Mar. 6, 1989, Pat. No. 4,895,719, which is a continuation-in-part of Ser. No. 737,221, May 22, 1985, abandoned.

[51] Int. Cl.⁵ .................... A61K 9/12; A61K 31/47
[52] U.S. Cl. ........................... 424/45; 424/450; 428/402.2; 514/169; 604/140
[58] Field of Search ............... 424/45, 450; 514/958, 514/959, 169; 604/140; 428/402.2; 264/4.1, 4.3, 4.6

[56] References Cited

U.S. PATENT DOCUMENTS

| | | | |
|---|---|---|---|
| 3,322,625 | 5/1967 | Shimmin | 167/54 |
| 3,594,476 | 7/1971 | Merrill | 424/199 |
| 3,933,822 | 1/1976 | Broughton et al. | 260/256.5 R |
| 4,211,771 | 7/1980 | Witkowski et al. | 424/180 |
| 4,232,002 | 11/1980 | Nogrady | 424/45 |
| 4,235,871 | 11/1980 | Papahadjopoulos et al. | 424/19 |
| 4,438,052 | 3/1984 | Weder et al. | 264/4.6 |
| 4,509,515 | 4/1985 | Altounyan et al. | 128/203.15 |
| 4,590,060 | 5/1986 | Ehrenfeld | 424/1.1 |
| 4,608,211 | 8/1986 | Handjani et al. | 264/4.6 |
| 4,624,251 | 11/1986 | Miller | 128/205.24 |
| 4,699,995 | 10/1987 | Buckle | 560/61 |
| 4,849,427 | 7/1989 | Nassim et al. | 514/291 |
| 4,895,719 | 1/1990 | Radhakrishnan et al. | 514/958 |
| 5,006,343 | 4/1991 | Benson et al. | 424/450 |
| 5,043,165 | 8/1991 | Radhakrishnan | 424/450 |

FOREIGN PATENT DOCUMENTS

| | | |
|---|---|---|
| 0084898 | 3/1983 | European Pat. Off. |
| 0158441 | 10/1986 | European Pat. Off. |
| WO86/01714 | 3/1986 | PCT Int'l Appl. |
| 8322178 | 9/1983 | United Kingdom |
| 2145107 | 3/1985 | United Kingdom |

*Primary Examiner*—Paul R. Michl
*Assistant Examiner*—G. S. Kishore

[57] ABSTRACT

A method for delivering a therapeutic dosage of corticosteroid drug to the lungs, for treating a lung condition or disease. An aqueous suspension of sized liposomes containing the drug in liposome-entrapped form is aerosolized under conditions which produce aerosol particle sizes favoring particle deposition in a selected region of the respiratory tract, and the aerosol is administered in an amount which delivers the thereapeutic dosage level to the selected lung region.

8 Claims, 2 Drawing Sheets

CORTICOSTEROID INHALATION TREATMENT METHOD

This application is a continuation in part application of copending application Ser. No. 022,937, filed Mar. 6, 1989, now U.S. Pat. No. 4,895,719, which is a continuation-in part application of copending parent patent application Ser. No. 737,221, filed May 22, 1985, now abandoned.

FIELD OF THE INVENTION

The present invention relates to drug delivery by inhalation, and, in particular, to a method for treating a lung condition or disease with a corticosteroid.

REFERENCES

"An Introduction to Experimental Aerobiology", Wiley, p 447 (1966).

Hollenbeck, R. G., et al., in "Pharmaceutics and Pharmacy Practice" (Banker, G. S., et al., eds), J. P. Lippincott, Philadelphia (1982), pp. 382-391.

Chamberlain, M. J., et al, Clin Sci, 64:69 (1983).
Goldberg, I., et al, Ann Biomed Engin, 9:557 (1981).
Morgan, A., et al, Br J Indus Med, 40:45 (1983).
Pityn, P. et al, Resp Phys, 78:19 (1989).

Remington's Pharmaceutical Sciences (Gannaro, A. R., Ed.), 17th edition, Mack Publishing Company (1985).

Scott, W., et al., J Aerosol Sci, 16:323 (1985).
Szoka, F., Jr., et al., Ann Rev BioPhys Bioeng (1980), 9:467.
Szoka, F., Jr., et al., Proc Natl Acad Sci (USA) (1978) 75:4194.
Yu, C., et al, J Aerosol Sci, 14:599 (1983).

BACKGROUND OF THE INVENTION

Inhalation provides an effective means for treating a variety of lung diseases and conditions, such as bronchial asthma, emphysema, bronchitis, and interstitial lung disease. An important advantage of inhalation in treating lung diseases is the ability to deliver the drug directly to the site of drug action. A related advantage is the rapid onset of the therapeutic effect, compared with other routes of administration, such as intramuscular and oral routes. For drugs which are susceptible to breakdown in the gastrointestinal tract, or which otherwise cannot be administered orally, inhalation may be preferred for a variety of reasons over intravenous or intramuscular injection.

In one known method for administering a drug by inhalation, the drug is dissolved in a suitable solvent which can be aerosolized to form a small-particle mist. That is, the drug is dissolved in an aerosol composed of a drug solvent. This approach is also referred to herein as a drug-solute method. Where the drug is relatively water-soluble, the drug can be dissolved in an aqueous medium which can be aerosolized, for example, by a pneumatic nebulizer. A lipid-soluble drug may be dissolved in a propellant solvent, such as a freon-type solvent, for metered-dose aerosolization from a self-contained pressurized cannister.

Inhalation of the aerosol mist, by drawing the mist from the mouth, acts to deposit the aerosol particles in the respiratory tract. In general, the site of deposition of the particles in the respiratory tract will depend on particle size, with smaller particles favoring deposition at lower respiratory-tract regions. For example, mist particle sizes of greater than about 2-3 microns are deposited predominantly in the upper regions of the respiratory tract, whereas particle sizes less than about 2 microns favor deposition in the lower pulmonary regions, including deep-lung or parenchymal lung sites (Pityn, Chamberlain, Morgan, Goldberg, Scott, Yu).

The drug-solute approach has limited utility for administering lipid soluble drugs, particularly to the deep lung region of the respiratory tract. Although a pneumatic nebulizer can be operated under conditions which produce aqueous aerosol particles in the desired size range between about 1-2 microns, the limited solubility of a lipid-soluble drug in an aqueous medium limits the amount of drug which can be delivered. A propellant-solvent aerosol, although capable of dissolving the drug at relatively high concentration, is generally unable to reach the deep lung, in part because of rapid evaporation of the solvent and concomitant change in aerosol particle size.

Also known in the prior art are inhalation systems in which a drug is administered in particulate form, as a micronized suspension in a suitable carrier solvent system. Typically, the drug is a water-soluble compound which is suspended in micronized form in a fluorocarbon-type propellant solvent. This approach is generally unsuited for delivery of a lipid-soluble drug because of the difficulty in producing micronized particles in the submicron size, such as are required for forming 1-2 micron aqueous aerosol particle sizes needed for delivery to the deep lung.

One class of lipid-soluble drugs which have a number of therapeutic applications in treating lung conditions includes the corticosteroids. Several corticosteroids, such as beclomethasone diproprionate (BDP), dexamethasone, prednisone, and flunisolide, are used in the treatment of bronchial asthma and related bronchoconstriction conditions. Typically, the steroid compound is administered orally, for systemic uptake, or by inhalation, using a propellant-solvent aerosolizing device.

Corticosteroids are also the drug of choice for treating interstitial lung diseases (ILD). ILD form a heterogeneous group of nearly two hundred diffuse, noninfectious, nonmalignant, inflammatory, and often fatal disorders of the lower respiratory tract, resulting in pathological changes of alveolar tissue, in particular alveolar septum, epithelial and endothelial cells. These diseases progress from the initial acute stage through semichronic to chronic stage and are characterized by progressive development of extensive lung fibrosis or granulomatosis.

Untreated, most ILD are progressive and may rapidly become fatal. The patient's condition deteriorates due to an irreversible loss of alveolar-capillary units, causing the right side of the heart to become hypertrophic due to increased load. The ultimate result is general respiratory insufficiency with decreased delivery of oxygen to vital tissues such as heart and brain and, eventually, death.

Conventional therapy of ILD includes oral or systemic administration of multidoses of anti-inflammatory corticosteroids. One commonly used therapy for ILD is 40-80 mg/day of prednisone orally for one to two months. To control symptoms in many ILD chronic cases, follow-up treatment with lower doses (5-15 mg/day prednisone) is needed for weeks, years, or indefinitely. Still, favorable responses to such massive doses of steroids are achieved in only 20-60% of patients. Moreover, the large doses of steroids required when the drug is administered orally or systemically are accompanied by severe side effects which may compromise the benefit of long-term treatment.

Administration of corticosteroids by the inhalation route has the potential for overcoming the serious limitations of current oral or IV corticosteroid therapy. In particular, direct drug delivery to the deep lung would be effective at relatively low doses, and thus substantially mitigate side effects seen with long-term therapy. However, the limitations discussed above for aerosolizing lipid-soluble drugs, particularly for delivery to the deep lung, have prevented effective inhalation therapy by the drug in free form heretofore.

SUMMARY OF THE INVENTION

It is therefore one general object of the present invention to provide an improved method for administering a corticosteroid drug to the respiratory tract.

A more specific object of the invention is to provide such method which can be readily adapted for delivery of a corticosteroid, at relatively high dosage level, to either the upper (bronchial) or deep-lung (alveoli) regions of the respiratory tract.

Parent patent application Ser. No. 737,121, filed May 22, 1985, now abandoned, discloses a liposome inhalation method for administering therapeutic agents in liposome-entrapped form to the lung. In one embodiment described in the parent application, the therapeutic agent is a corticosteroid, such as dexamethasone or beclomethasone. The liposomes are formed as an aqueous suspension and are sized to have substantially homogeneous sizes less than about 0.5 microns, preferably about 0.2 microns. The aqueous suspension is aerosolized under conditions which produce aerosol particle sizes favoring particle deposition in a selected region of the lung. Particle sizes greater than 2-3 micron favor deposition in the upper respiratory tract, for example, for treating bronchoconstriction, and sizes less than about 2 micron favor deposition in the lower pulmonary regions, for treating interstitial lung diseases.

In a preferred embodiment, the aerosol particles are formed by a pneumatic nebulizer. The liposomes may be formulated to contain steroidal components, such as cholesterol sulfate and cholesterol, to produce delayed release of the corticosteroid from the site of liposome deposition in the respiratory tract.

Newly disclosed in the present application is a novel liposome formulation containing predominantly steroidal components, such as a combination of cholesterol and cholesterol sulfate, for producing delayed release of corticosteroid from the liposomes in the lung environment. This embodiment of the present invention is related to the novel liposome formulation disclosed in co-owned patent application for "A Novel Liposome Composition for Sustained Release of Steroidal Drugs in the Lungs", Ser. No. 284,158, filed Dec. 14, 1988.

These and other objects and features of the present invention will become more fully apparent when the following detailed description of the invention is read in conjunction with the accompanying drawings.

DETAILED DESCRIPTION OF THE INVENTION

Forming an Aqueous Liposome Suspension

Figure 1:
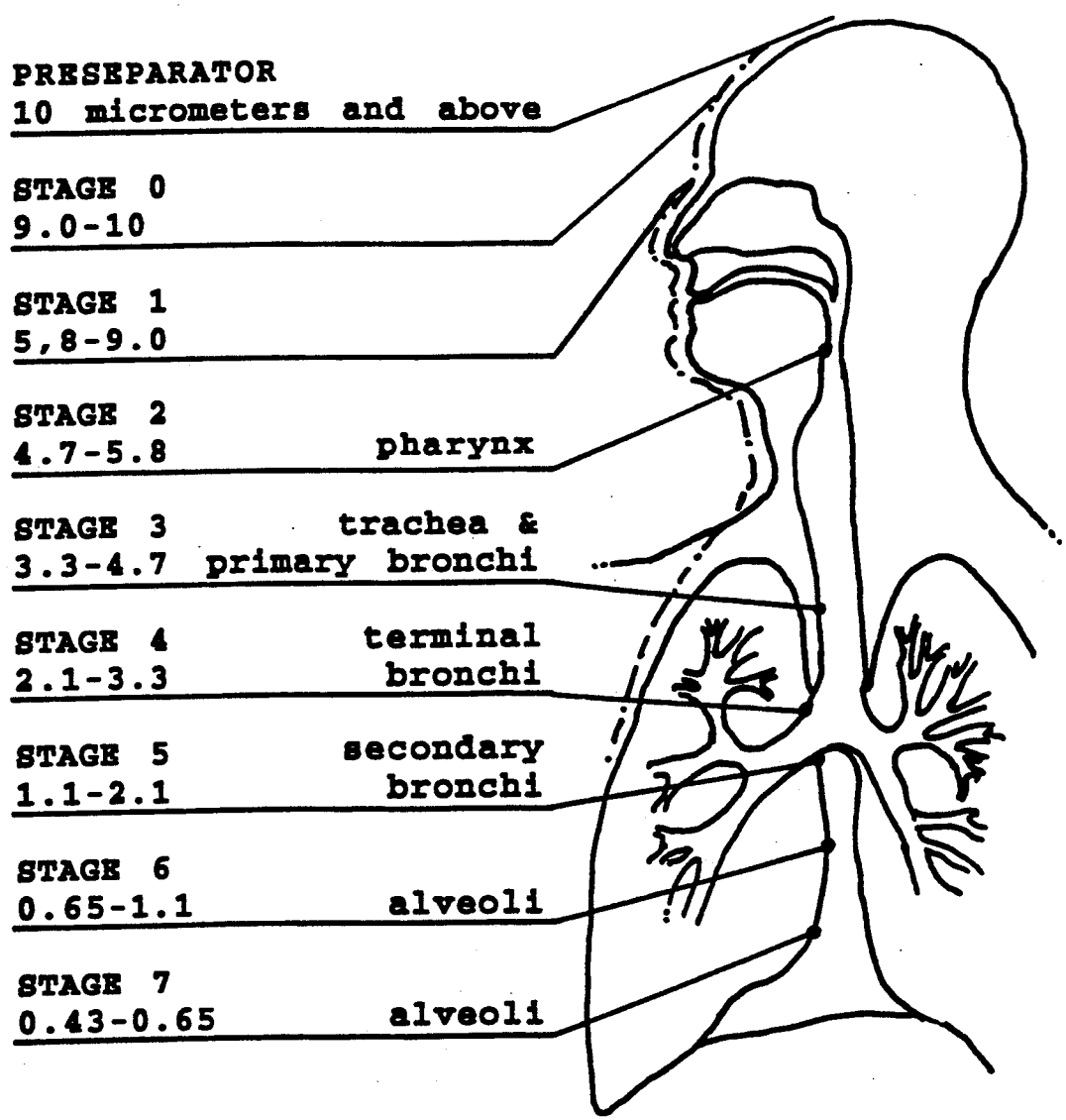
FIG. 1 shows depicts the regions of the human respiratory tract corresponding to the stages of an Anderson cascade impactor.

The liposomes of the present invention are formulated to include a selected corticosteroid drug, defined herein as any steroid produced by the adrenocortex, including glucocorticoids and mineralcorticoids, and analogs and derivatives of naturally occuring corticosteroids having an anti-inflammatory activity. Exemplary corticosteroids include, but are not limited to, aldosterone, beclomethasone, betamethasone, budesonide, cloprednol, cortisone, cortivazol, deoxycortone, desonide, dexamethasone, difluorocortolone, flucloronone, fluorocortisone, flumethasone, flunisolide, fluocinolone, fluocinonide, fluorocortolone, fluorometholone, flurandrenolone, fluticasone, halcinonide, hydrocortisone, meprednisone, methylprednisolone, paramethasone, prednisolone, methylprednisolone, prednisone and triamicinolone, and their respective pharmaceutically acceptable salts or esters, such as beclomethasone diproprionate.

The lipid components used in forming the liposomes of the invention may be selected from a variety of vesicle-forming lipids, typically including phospholipids and sterols. The phospholipid components typically include neutral phospholipids, such as phosphatidylcholine (PC) and negatively charged phospholipids, such as phosphatidylglycerol (PG), phosphatidic acid (PA) or phosphatidylinositol (PI). The sterol typically is cholesterol. The formulation described in Example 1 is composed of partially hydrated egg PC (PHEPC), egg PG (EPG), beclomethasone dipropriate (BDP), and alpha-tocopherol, in a mole ratio of 95:3:2:0.1. More generally, the preferred formulation is composed of 30–95 mole percent PC, 3–20 mole percent PG, 20–50 mole percent cholesterol, and between about 0.1 to 2 mole percent corticosteroid drug.

The lipids making up the bulk of the vesicle-forming lipids in the liposomes may be either fluidic lipids, e.g., phospholipids whose acyl chains are relatively unsaturated, or more rigidifying membrane lipids, such as highly saturated phospholipids. In particular, the vesicle-forming lipids may be selected to achieve a selected degree of fluidity or rigidity, for example, to achieve desired liposome preparation properties. It is generally the case, for example, that more fluidic lipids are easier to formulate and size by extrusion than more rigid lipid components.

The liposomes may be formulated to produce delayed release of the corticosteroid from the liposomes, by forming the liposomes predominantly of steroidal components, such as cholesterol and the salt of a choesterol acid, such as cholesterol sulfate. In this embodiment, the liposomes are formulated to include, as vesicle-forming lipids, more than 50, and preferably up to 80–95% mole percent steroidal components, and the remainder phospholipid, such as PC, and corticosteroid drug. In one preferred formulation relating to this embodiment, the liposomes include 30–70 mole percent cholesterol sulfate, 20–50 mole percent cholesterol, 5–20 mole percent neutral phospholipid, and between 0.01 to 10 mole percent corticosteroid drug. The ability of cholesterol and cholesterol acid component to produce delayed release of steroidal drugs in liposomes is described in co-owned, co-pending U.S. patent application Ser. No. 284,158, filed Dec. 14, 1988, now U.S. Pat. No. 4,906,476, Mar. 6, 1990, which is incorporated herein by reference.

The liposomes may be prepared by a variety of preparative methods. In the solvent-injection method described in Example 1A, lipid-vesicle components and corticosteroid drug are dissolved in a suitable lipid solvent, such as a freon solvent, and injected into an aqueous medium, such as phosphate buffered saline, until a desired lipid concentration in the liposome suspension is reached, preferably between about 10–100 μmole/ml, and more preferably about 40 μmole/ml. The quantitative composition of the resulting liposomes is shown in Table 1 in this example.

Another preferred procedure is based on hydration of a lipid film, to form multilamellar vesicles (MLVs). In this procedure, a mixture of liposome-forming lipids of the type detailed above, including the selected corticosteroid drug, are dissolved in a suitable solvent, and the lipid solution is evaporated in a vessel to form a thin film, which is then covered by an aqueous medium. With addition of a suitable aqueous medium, such as the above phosphate buffered saline medium, the lipid film hydrates to form MLVs, typically with sizes between about 0.1 to 10 microns. As above, aqueous medium is preferably added to a final lipid concentration of between about 10–100 μmole/ml, and preferably about 40 μmole/ml.

This lipid hydration method is described in example 1B, for the preparation of a predominantly phospholipid liposome suspension, and in Example 2, for a predominantly steroidal liposome suspension. It will be understood that other liposome-preparation methods for producing liposomes (as described, for example, in Szoka et al, 1980) may also be employed.

The aqueous suspension of liposomes is prepared to have liposome sizes less than about 0.5 microns, and preferably about 0.2 microns or less. This relatively small size is necessary for forming small aerosol particle sizes, such are required for reaching the lower pulmonary region of the respiratory tract. A variety of methods are available for producing liposomes with relatively small sizes, or, alternatively for sizing larger, heterogeneous-size liposomes. Liposome sizes of about 0.2 microns or smaller also can be sterilized readily, by filtration through a conventional 0.25 micron depth filter.

In one preferred liposome sizing method, the liposomes are extruded through a polycarbonate membrane having a selected uniform pore size, typically 0.05, 0.08, 0.1, 0.2, or 0.4 microns (Szoka, 1978). The pore size of the membrane corresponds roughly to the largest sizes of liposomes produced by extrusion through that membrane, particularly where the preparation is extruded two or more times through the same membrane. In a more recently described method, an unsized liposome suspension is extruded through an asymmetric ceramic filter. The method is detailed in U.S. patent application for Liposome Extrusion Method, Ser. No. 829,710, filed Feb. 13, 1986.

Alternatively, unsized liposomes, such as the REV or MLV preparations above, can be treated to produce small unilamellar vesicles (SUVs) which are characterized by sizes in the 0.04–0.08 micron range. Because of the small particle sizes, SUVs are particularly suitable for the delivery of steroid to the alveoli. Another advantage of SUVs, for treatment of deep lung diseases, is the greater packing density of liposomes at a mucosal surface.

Although SUVs are conducive to formation of small aerosol particles, they have a substantially lower drug-carrying capacity than larger sized liposomes, e.g., liposomes in the 0.1–0.2 micron size range. For this reason, larger liposomes, in the 0.1 to 0.2 micron size range, are generally preferred.

After final sizing, the liposomes can be treated, if necessary, to remove free (non-entrapped) corticosteroid drug. Conventional separation techniques, such as centrifugation, diafiltration, and molecular-sieve chromatography are suitable. The composition can be sterilized by filtration through a conventional 0.25 micron depth filter. The final concentration of corticosteroid in the sized-liposome suspension is preferably between about 0.1 and 2 mg/ml. One preferred drug concentration, in a liposome suspension containing 40 μmole/ml lipid, is 0.4–0.5 mg/ml corticosteroid drug.

Aerosolizing the Sized Liposome Suspension

In the treatment method of the invention, the aqueous suspension of sized liposomes, prepared as above, is aerosolized under conditions which produce aerosol particle sizes favoring aerosol particle deposition in the selected region. Aerosol particle size and the relationship of size to site of deposition in the respiratory tract can be examined by the Anderson impactor device for simulating the human respiratory system. The impactor device is divided into seven segments, which are separated from one another by screen filters with the following pore sizes: 10 μ and above-preseparator stage, 9–10 μ-Stage 0; 5.8–9 μ-Stage 1; 4.7–5.8 μ-Stage 2; 3.3–4.7 μ-Stage 3; 2.1–3.3 μ-Stage 4; 1.1–2.1 μ-Stage 5; 0.65–1.1 μ-Stage 6; and 0.43–0.65 -μ Stage 7. A suitable filter is placed at the end to collect any submicronic droplets.

FIG. 1 shows the regions of the respiratory tract which correspond to the seven stages in the Anderson impactor, and the droplet sizes selected at each stage. As seen, the three lower regions of the respiratory tract, encompassing the terminal bronchi and alveoli, are reached by particles whose sizes are between about 0.43 and 0.65 micron (stage 7 alveoli), 0.65 and 1.1 micron (stage 6 alveoli) and 1.1 and 2.1 microns (terminal bronchi). Thus, in treating ILD by the method of the invention, aerosol particle sizes between about 0.4 and 2.1 microns are produced. Similarly, treatment directed to the upper respiratory tract, such as in treating bronchial asthma with corticosteroids, will require particles with sizes between about 2.1 and 4.7 micron. The effect of particle size on particle deposition in the human lung has also been reported in several other studies (Pityn, Chamberlain, Morgan, Scott, Goldberg, Yu).

Aerosol particle size (in microns) herein refer to mass median aerodynamic diameter (MMAD), defined as the particle diameter for which half of the mass of the aerosol is contributed by particles larger than the MMAD, and half, by particles smaller that the MMAD ("Introduction to Experimental Aerobiology").

One preferred device for producing desired-size aerosol particles is a pneumatic nebulizer. In the usual aerosolizing procedure, the aqueous liposome suspension is placed in the nebulizer, and compressed air is supplied to the nebulizer. The pressurized air forces the liposome suspension through a nozzle having a defined size orifice, producing a predominantly coarse-particle aerosol. This aerosol is then directed against a baffle which traps larger aerosol particles and passes smaller ones. The size of the aerosol particles which are produced can be selectively varied, according to well-known nebulizer operation, by changes in pressure, nozzle orifice size, and baffle screen dimension.

For producing particle sizes suitable for delivery to the deep-lung, i.e., with particles sizes less than about 1-2 microns, a single-use ultravent nebulizer supplied by Mallinckrodt (St. Louis, Mo.) or a Respigard II TM nebulizer Marquest (Englewood, Colo.) are suitable.

Figure 2A:
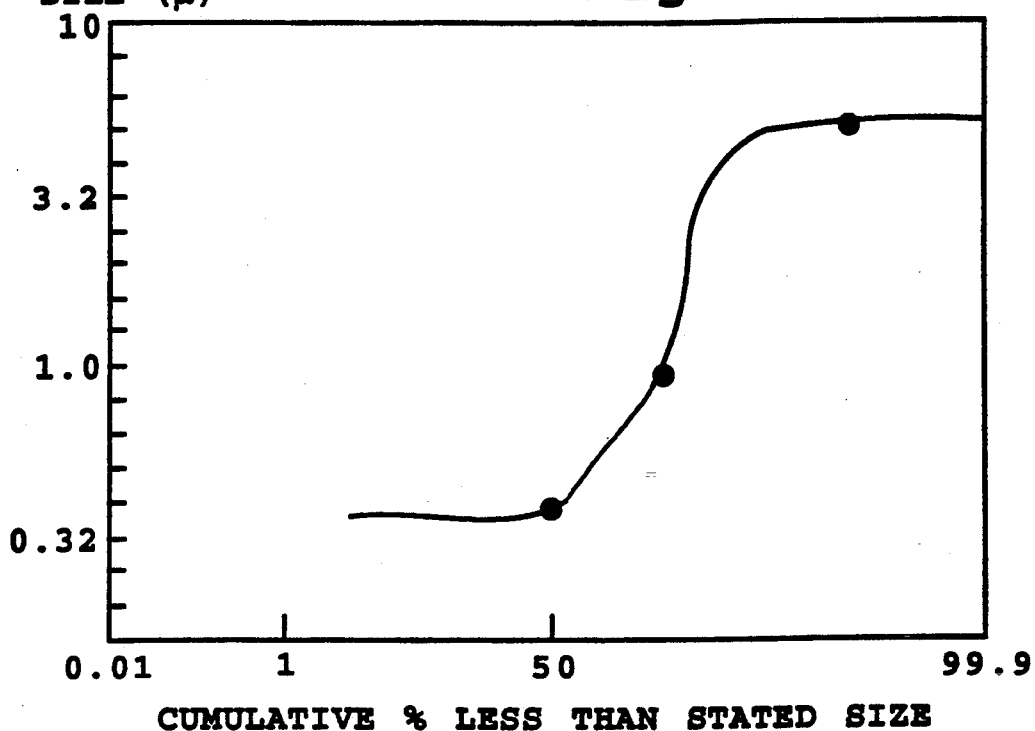
FIGS. 2A and 2B show plots of cumulative percent mass of aerosolized particles less than the stated size, as a function of aerosol particle size, for aqueous aerosols produced by two exemplary pneumatic nebulizers.
Figure 2B:
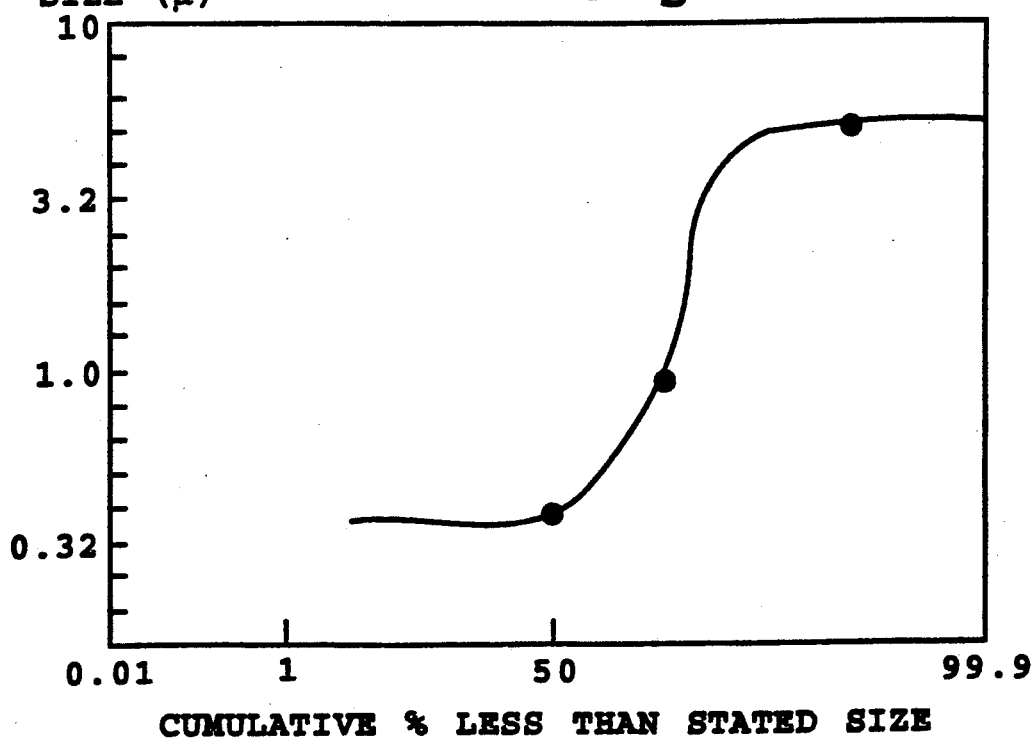

FIG. 2A shows the liquid aerosol particle size distribution of a suspension of 0.2 micron liposomes, prepared as in Example 1, using the Respigard II TM nebulizer at an airflow of 28 L/min. Each point on the plot was determined from the liposome mass present at each stage of the Anderson impactor, as described in Example 2. As seen from the plot, 50% of the particle mass is less than 0.42 microns (MMAD diameter), and only about 15% of the particles are greater than 2 microns. Similar results were achieved in a liposome suspension nebulized under similar conditions with the Mallinckrodt nebulizer (FIG. 2B). The Andersen cascade impactor used in the study was obtained from Andersen Air Sampler, Inc. (Atlanta, Ga.); a QCM Cascade impactor was obtained from California Measurements (Sierra Madre, Calif.).

It has earlier been shown (patent application Ser. No. 737,221) that the pneumatic nebulizing process does not significantly affect liposome integrity and size, as judged by change in particle size or loss of a water-soluble encapsulated reporter molecule from four liposome preparations with different levels of lipid saturation. No change in liposome size or loss of encapsulated material was observed for three of the preparations, and only a slight loss of encapsulated material and moderate increase in size was observed for liposomes with the most saturated lipid components.

Another device suitable for aerosolizing an aqueous suspension of liposomes, and preferably a relatively dilute suspension containing less than about 25%-30% encapsulated aqueous volume, uses ultrasonic energy to break up a carrier fluid into a fine mist of aqueous particles. One ultrasonic device which was used was found to produce a liposome aerosol mist whose particle sizes are between about 2-6 microns, and is thus useful for generating particle sizes designed for liposome deposition in the upper respiratory tract, such as for treatment of bronchial asthma and related bronchoconstriction conditions.

Therapeutic Applications

As indicated above, the method of the invention is applicable both to the treatment of bronchial constriction conditions, and interstital lung disease with corticosteroid therapy, depending on the size of aerosol particles which are administered by inhalation.

In the treatment method for bronchial constriction, a suspension of sized liposomes containing corticosteroid in liposome-entrapped form is prepared as above. Exemplary corticosteroids which may be employed include beclomethasone, betamethasone, budesonide, dexamethasone, flunisolide, fluticasone, and triamcinolone. The liposomes may be predominantly phospholipid vesicles containing up to about 2 mole percent drug, as described above, or vesicles composed predominantly of steroid components, such as cholesterol and cholesterol sulfate, and containing up to about 10 mole percent corticosteroid compound, for achieving delayed release of the drug, as detailed in co-pending, co-owned patent application Ser. No. 284,158, filed Dec. 14, 1988 now U.S. Pat. No. 4,906,476.

The desired daily dose of corticosteroid is preferably about 0.4 to 2 mg drug, depending on the drug selected, as can be determined from the Physician's Desk Reference (1988). According to one advantage of the invention, the effective daily dose can be administered readily as a single dose, and thus avoid the multiple dosing required in current propellant inhalation systems for administering corticosteroids.

In one exemplary treatment method, the total daily drug amount which is administered placed in the nebulizer is about 4 times the desired daily dose, since only about 25 percent of the nebulized suspension will be inhaled and reach the target lung site (according to the above Anderson analysis, and taking into account that a large portion of the aerosol will be swallowed or otherwise not inhaled). Typically, the nebulizer cup will be loaded with about 4 ml of the suspension, and this will be inhaled by the patient over a 20-30 minute aerosolization period. Thus, for example, to administer a 0.2 mg dose of a corticosteroid, 4 ml of a liposome suspension containing about 0.2 mg drug per ml is loaded into a nebulizer, and the suspension is aerosolized over a 20-30 minute period, under conditions which produce aerosol particles greater than about 2 microns MMAD. The aerosol is administered to the patient by inhalation, i.e., inhaled by the patient, during the aerosolization period, with the total amount reaching the upper respiratory tract being approximately 0.2 mg. Of course, the dosage can be reduced, if desired, by diluting the suspension added to the nebulizer, or reducing inhalation time.

The treatment method for ILD follows the same general procedures described above, except that the nebulizer is operated under conditions which produce aerosol particle sizes having a MMAD of less than about 2.1 $\mu$, as detailed above. Exemplary corticosteroids which are useful for the treatment of ILD include prednisone, prednisolone, and methylprednisolone. The drug concentration in the liposome suspension, and method of aerosol administration is determined as above.

The deep-lung treatment method is useful for a broad range of ILD, including idiopathic pulmonary fibrosis and pulmonary sarcoidosis. The corticosteroid is preferably administered daily, at a dose level between about 0.2 to 2 mg, depending on the drug selected. The relatively low doses of drug which are possible with direct drug administration to the lower respiratory tract, in contrast to the doses required with oral administration, significantly reduce the possibility of severe long-term side effects associated with current treatment methods. At the same time, the higher concentration of corticosteroid which is possible at the alveolar target site with direct inhalation delivery provides greater treatment efficacy.

The advantage of the ILD treatment method of the invention over systemic administration can best be illustrated by a potent anti inflammatory steroid dexamethasone. Doses of dexamethasone administered systemically by i.v. injection typically range between 0.5 to 9 mg/day. Where, however, dexamethasone is administered via inhalation, the corresponding effective daily inhalation dose for dexamethasone is from 0.4 to about 1.0 mg/day. PDR: 1311, 1312 and 1315 (1988).

From the foregoing, it can be appreciated how various objects and features of the invention are met. In the treatment of upper respiratory lung conditions with corticosteroids, the invention provides the advantage over drug-solute aqueous inhalation methods, in that the drug concentration in the aqueous medium can be made relatively high, and thus allow effective daily dosing on a once-a-day basis.

The method of the invention has the advantage over particle suspension aqueous media, for treatment of bronchial conditions, in that particle-irritation effects, and problems of large aerosol particles, which can prevent a sizable portion of the aerosol medium from reaching the brochii. The method has the advantage over drug-solute propellant solvent mixtures in avoiding solvent irritation effects, and poor control over particle size.

For treatment of ILD, the method allows for the delivery of relatively large drug doses to the lower respiratory tract, in contrast to drug-solute aqueous systems, where low drug solubility limits the amount of drug which can be delivered. Drug-solute propellant systems, which have the potential for high drug dose delivery, are unsuited for delivery to the deep lung, for the reasons discussed.

The following examples illustrate methods of preparing sized liposome suspensions suitable for use in the invention, and for testing the size distribution of liposome-containing aerosol particles formed by pneumatic nebulization, for use in drug delivery to the deep lung. The examples are intended to illustrate, but in no way to limit, the scope of the invention.

Materials

Beclomethasone dipropionate (BDP) and α-tocopherol (α-T) were obtained from Sigma Chemical Co. (St. Louis. Mo.); Partially hydrogenated egg phosphatidyl choline (PHEPC) and egg PG (EPG) were from Austin Chem. Co., Inc. (Rosemont, Ill.); cholesterol was from Croda (Mill Hall, Pa.); and cholesterol sulfate was from Genzyme Corp. (Boston, Mass.)

EXAMPLE 1

Preparation of Phospholipid Liposome Suspensions

Solvent Injection Method

A mixture of PHEPC, EPG, cholesterol, BDP, and alphatocopherol, in a mole ratio of 95:3:2:0.1 were dissolved in 100 ml of Freon 11 containing 1.0 ml of ethanol, to a lipid concentration of about 20 mM. A liposome/BDP suspension was formed by slowly injecting the lipid/drug/freon solution into 50 ml of the phosphate buffered saline pH 7.4 (pH 7.4, mOsm- 295, originally preserved with sodium azide) under the following conditions: Injection rate: 1.25 ml/min; Vacuum: 400 mm Hg; Temperature: 20° C.; Mixer rate 1000 rpm. After the injection was completed, the vacuum level was adjusted to 150 mmHg for about 30 min to remove residual solvent.

The liposomes formed in the 50 ml suspension were sized by successive extrusion through a 0.4 or a 0.2 micron polycarbonate membrane, to produce a uniform size liposome distribution and to remove free drug crystals.

The composition of the suspension was calculated and/or assayed, with the results given below in the middle and right columns in Table 1, respectively. The physicochemical characteristics of the liposome suspension are summarized in Table 2.

TABLE 1

Quantitative Composition of BDP Liposome (Solvent Injection Batch No. 457-KF-57EX)

| Ingredient | Nominal Concentration mg/mL | Assay |
|---|---|---|
| Egg Phosphatidylcholine 95% (partially hydrogenated) IV-40 | 29.6 | 34* |
| Egg Phosphatidylglycerol 95% | 0.9 | N.D. |
| Beclomethasone dipropionate USP | 0.42 | 0.40 |
| Vitamin E (dl-alpha-Tocopherol) | 0.172 | N.D. |
| Monobasic Sodium Phosphate (monohydrate) | 1.5 | N.D. |
| Dibasic Sodium Phosphate (heptahydrate) | 11.5 | N.D. |
| Sodium Chloride | 5.0 | N.D. |
| Deionized water qs to 1.0 mL | | |

Formulation Code:
PHEPC:EPG:BOT:α + T 95:3:2:0.1 Solvent Injection/457-KF-57/50 mL
*assume an average phospholipid MW of 763.5

TABLE 2

Physicochemical Characteristics of BOP Liposomes (Solvent Injection Batch No. 457-KF-57EX)

| Characteristics | Assay |
|---|---|
| Visual Appearance | Milky Suspension |
| Odor | Characteristic No Rancidity |
| Particle Size (Liposomes) | 257 nm (NICOMP) dispersity 34% |
| Drug Concentration | 0.41 mg/mL (UV) |
| pH | 7.3 |
| Osmolality | 293 mOsm/kg |
| Residual Ethanol | >500 ppm |
| Residual Freon | None detected |
| Phospholipid Assays | |
| PC | 95.8% |
| PG | 2.0% |
| LPC | 0.3% |

B. Thin-Film Hydration Method

About 2 mmole of the lipid mixture from part A above were dissolved in 5 ml of chloroform, and the solution was dried to a thin film in a round bottom flask. The film was hydrated by addition of 50 ml phosphate buffered saline, pH 7.4, with agitation for 2 hours at room temperature. The liposomes formed in the 50 ml suspension were sized by successive extrusion through a 0.4 or a 0.2 micron polycarbonate membrane, as above.

EXAMPLE 2

Preparation of Steroidal Liposome Suspension

A lipid mixture containing PHEPC, cholesterol sulfate, cholesterol, and BDP, in a mole ratio of 1:5:4:1 is dissolved in 10 ml methanol:chloroform (2:1), added to a screw-cap test tube and dried under nitrogen. The procedure is repeated three times and the dried film was lyophilized for half an hour at room temperature. Depending on the liposomal volume needed, the residue is resuspended in about 2 to 5 ml of phosphate buffered saline and sonicated with a bath sonicator (Model G112SP1T, 600 volts, 80 KC, .05 Amps) for half an hour to prepare multilamellar vesicles (MLVs). An aliquot of the sonicated, pre-extruded MLVs sample is saved and volume of preparation recorded for determination of baseline values. The suspension is extruded with through a 8.0 μ Nucleopore polycarbonate membrane and two times through a 0.4 um Nucleopore polycarbonate membrane.

A post-extrusion sample is saved to determine the amount of drug or lipid lost in the sizing process. Post-extrusion volume was noted. Free drug, if any, is removed by repeated washing with phosphate buffered saline and centrifugation. Liposomes are centrifuged three times on the Beckman L8-70M Ultracentrifuge at temperature of 4° C., at 47,600 rpm, for 1 hour, using 50 Ti rotor. The supernatant is discarded and the pellet resuspended in a volume equal to the post-extrusion volume after each centrifugation.

EXAMPLE 3

Size Distribution of Liposome Aerosol Particles

The liposome suspension prepared as in Example 1A was added (4 ml) to the liquid Cup of a single-use ultravent nebulizer obtained from Mallinckrodt (St. Louis, Mo.).

The liposome suspension was aerosolized in the nebulizer at an air pressure of 10 psi, and the aerosol particles were directed into an Anderson cascade compactor obtained from Anderson Air Sampler (Atlanta, Ga.) at an air flow velocity of 28 L/min. The particle retention size limits of each of the seven stages in the compactor are given in Section II above. The aerosol was directed into the compactor for 20 minutes, and at the end of this period, some of the original 4 ml sample remained in the nebulizer. The amount of liposome suspension material which collected on the glass slide in each stage was quantitated by determining total BDP in the sample spectrophotometrically, by absorbance at 239 nm.

The amount of lipid suspension, expressed as the cumulative percent less than the stated size was plotted as a function of particle size, with the results shown in FIG. 2A. The particle size value in the graph is approximately the average or intermediate value between the two size limitations in each compactor stage. The MMAD value, determined from the 50% value, is about 0.42 microns.

A similar particle size study was carried out with an aerosol produced by a single-use Respigard II nebulizer obtained from Marquest (Englewood, Colo.), with the results shown in FIG. 2B. The MMAD value determined from this experiment is about 0.44.

Also as seen from the two FIG. 2 plots, more than 90% of the total particle mass has sizes less than 1 micron, showing that either nebulizer is suitable for use producing an aerosol suitable for deep-lung treatment.

Although preferred embodiments of the invention have been described herein, it will be appreciated that various changes and modifications may be made without departing from the invention.

What is claimed is:

1. A method for administering a therapeutic dose of a corticosteroid to the respiratory tract, for treatment of a condition or disease of the respiratory tract, comprising
   (a) preparing an aqueous suspension of liposomes having sizes less than about 0.5 microns and containing the corticosteroid in entrapped form,
   (b) aerosolizing the suspension in a pneumatic nebulizer under conditions which produce aerosol particle sizes in the range between about 0.4 and 6 microns, favoring aerosol particle deposition in the respiratory tract, and
   (c) administering by inhalation, a quantity of the aerosol containing such therapeutic dosage of the corticosteroid in liposome-entrapped form.

2. The method of claim 1, wherein said corticosteroid is selected from the group consisting of aldosterone, beclomethasone, betamethasone, cloprednol, cortisone, cortivazol, deoxycortone, desonide, dexamethasone, difluorocortolone, fluclorolone, fluorocortisone, flumethasone, flunisolide, fluocinolone, fluocinonide, fluorocortolone, fluorometholone, flurandrenolone, halcinonide, hydrocortisone, meprednisone, methylprednisolone, paramethasone, prednisolone, prednisone and triamcinolone, and their respective pharmaceutically acceptable salts or esters.

3. The method of claim 2, wherein the corticosteroid is selected from the group consisting of beclamethasone and dexamethasone and their pharmaceutically acceptable salts or esters.

4. The method of claim 1, wherein the steroidal drug is beclomethasone dipropionate.

5. The method of claim 1, for use in treating bronchial asthma or a related bronchoconstriction condition, wherein the said aerosolizing includes producing aerosol particles in the 2-6 micron particle size region.

6. The method of claim 1, for use in treating interstital lung disease, wherein the said aerosolizing includes producing aerosol particles having sizes less than about 2 microns.

7. A method for administering a therapeutic dosage of a corticosteroid to the lower pulmonary region of the respiratory tract, for treatment of deep-lung disease, comprising
   (a) preparing an aqueous suspension of liposomes having sizes less than about 0.5 microns and containing the corticosteroid in entrapped form,
   (b) aerosolizing the suspension in a pneumatic nebulizer under conditions which produce aerosol particle sizes in the range between about 0.4 and 2.1 microns which favor deposition of the aerosol particles in the lower pulmonary regions of the respiratory tract, and
   (c) administering by inhalation, a quantity of the aerosol containing such therapeutic dosage of the corticosteroid in liposome-entrapped form.

8. The method of claim 7, wherein the aerosol particles have a mass median aerodynamic diameter less than about 2.1 microns.

* * * * *